United States Patent [19]

Christensen et al.

[11] Patent Number: Plant 6,714

[45] Date of Patent: Apr. 4, 1989

[54] HYBRID TEA ROSE PLANT CV. AROBIPY

[75] Inventors: Jack E. Christensen, Ontario; Thomas F. Carruth, Canoga Park, both of Calif.

[73] Assignee: Bear Creek Gardens, Inc., Somis, Calif.

[21] Appl. No.: 117,615

[22] Filed: Nov. 5, 1987

[51] Int. Cl.[4] ..... A01H 5/00

[52] U.S. Cl. ..... Plt./14

[58] Field of Search ..... Plt./36

*Primary Examiner*—Robert E. Bagwill

*Attorney, Agent, or Firm*—Majestic, Gallagher, Parsons & Siebert

[57] ABSTRACT

This invention relates to a new and distinct variety of hybrid tea rose plant cv. Arobipy, particularly suited for cut flowers and garden decoration, identified by its large white flowers with a hint of green along the midrib and pink on the margin of the outer guard petals.

1 Drawing Sheet

1

The present invention relates to a new and distinct variety (cv. Arobipy) of rose plant of the hybrid tea class. The plant is a tall growing, hardy greenhouse seedling with large white flowers, cultivated for cut flowers and garden decoration. It was first originated by Thomas F. Carruth and Jack E. Christensen in Ontario, Calif., U.S.A. under conditions of careful control and observation, and has as its seed parent the floribunda rose, Bridal Pink (U.S. Plant Pat. No. 2,851), and as its pollen parent, an unnamed grandiflora rose identified by Armstrong Roses of Somis, Calif., U.S.A. as No. 78100-A-5.

The new rose cv. Arobipy is particularly distinguishable from other commercialized rose cultivars by the following combination of characteristics: its tall growing habit and its large, excellently-formed buds and flowers; its uniformly white blossoms with only the outer guard petals having traces of pink and green along the margin and midrib, respectively; and its broad petals numbering about 30 to 35 petals per blossom.

In comparison to White Masterpiece (U.S. Plant Pat. No. 2,998), Arobipy has a significantly longer flower stem. The flowers of Arobipy bear fewer petals than White Masterpiece; petals of White Masterpiece are narrower than those of Arobipy. Arobipy has better petal color in the bud than White Masterpiece.

Arobipy holds its distinguishing characteristics through succeeding propagation by budding cuttings and in vitro propagation.

The new variety cv. Arobipy may be distinguished from its seed parent, Bridal Pink by the following combination of characteristics: Whereas Bridal Pink is a floribunda rose, Arobipy is a hybrid tea rose. The petal color of Arobipy is white; only the outer guard petals have traces of pink and green along the margin and midrib, whereas the petal color of Bridal Pink is pink. Bridal Pink has an average stem length of between about 38 to about 50 cm. whereas the average stem length of Arobipy is between about 50 to about 66 cm.

The new variety may be distinguished from its pollen parent, 78100-A-5, by the following combination of characteristics: Whereas the flower color of 78100-A-5 is lavender, the flower color of Arobipy is white as described above. Blossoms of Arobipy have about 30 to 34 petals whereas blossoms of 78100-A-5 have fewer petals, about 23 to 25 on the average Arobipy is much more vigorous than 78100-A-5.

2

The accompanying drawing illustrates the new variety in color as grown in Somis, Calif., and shows the flowering thereof from bud to full bloom.

The descriptive matter which follows pertains to roses of the new variety grown in the greenhouse in Somis, Calif., and is believed generally to apply to plants grown under similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWER

The new variety usually bears its flowers singly, sometimes two to three to a stem. Flowers are borne in rounded to irregular clusters on strong stems that are long for the class. In the greenhouse and outdoors, the plant blooms in moderate abundance and continuously during the growing season. Blooms have a moderate tea fragrance.

BUD

The peduncle is of average length for the class, of average caliper, strong and erect. The peduncle is smooth with some stipitate glands. Bud color is near Green 144B.

Before the calyx breaks, the bud is medium in size for the class, of medium length, pointed and ovoid in form with a conspicuous neck. There are foliaceous appendages and stipitate glands on the surface of the bud, with deeply serrate foliaceous parts extending beyond the tip of the bud and equal to or 1½ times its length.

As the calyx breaks, bud color is near Green 143A.

The inner surface of the sepals is lined with a fine wooly tomentum. Sepal margins are lined with stipitate glands and hairs.

As the first petal opens, buds are large in size for the class, long and urn-shaped in form. Color of the outside and inside of the bud petals is between near Green-White 157D and White 155D.

The bud opens up well and is not prevented from opening by cold, hot, wet or dry weather.

BLOOM

The size of the bloom when fully open is average to large for the class, about 5 inches to about 5½ inches in diameter. Petalage is very double, averaging from about 30 to about 34 petals arranged regularly, plus 1 or 2 petaloids.

Blooms at one half open are high-centered in form, with cupped petals. Petal edges are somewhat rolled outward.

When fully open, the blooms are somewhat cupped, with cupped petals and petal edges slightly reflexed outward.

The petals are of moderatley heavy substance, of medium thickness, slightly satiny on the inside surface and on the outside surface. Outside petals are broadly obovate in shape with rounded apices, usually without notches. Intermediate petals are broadly obovate in shape with rounded apices and usually bear zero to one notch. Inside petals are broadly obovate, sometimes scalloped, with rounded apices and usually bear zero to one notch.

Colors may be modified by being margined or tinted with other colors.

The following paragraph describes the color values observed in a newly opened flower from a plant of the new variety grown in a greenhouse in Somis, Calif. in June of 1987.

The outside surface of the outside, intermediate and inside petals is near White 155A. The inside surface of the outside, intermediate and inside petals is near White 155B.

The general color effect of the newly opened flower is near White 155A with a tinge of light green near the veins and midrib of the outer petals. The outer petals may have a light pink margin, near Red 49C.

The following paragraph describes the color values observed in a flower open for three days indoors from a plant of the new variety in October, 1987 at Somis, Calif.

The color of the outside and inside surface of both the outside and inside petals is between Yellow-White 158C and White 155C.

After being open three days, the general color effect of the flower is similar to that described for newly opened flowers but with much less pink or green coloring.

Petals usually drop off cleanly and are not particularly affected by cold, hot, wet or dry weather.

Flowers grown in the month of May last on the bush in the garden from 6 to 7 or more days. Cut flowers from rose plants grown in the greenhouse or outdoors last from 4 to 5 days in May when kept at living room temperature.

REPRODUCTIVE ORGANS

Stamens are average to many in number and are arranged regularly about the pistils; a few may also be mixed with petaloids. Filaments are short to medium in length and most have medium sized anthers. Anthers open approximately all at once. Mature anthers are Yellow-Orange 19A in color; immature anthers are Yellow-Orange 18A in color. Pollen is produced in moderate quantities and is Yellow-Orange 19A in color.

Pistils are average in number for the class (about 30). Styles are average to long in length, of thin to average caliper, and are somewhat loosely bunched. Stigma color is near Yellow 10B. Some ovaries are enclosed in the calyx and some protrude from the calyx.

Hips of the variety are of average length and ovoid to oblong to globular in shape. Hips are smooth in texture and near Orange-Red 34B in the center and near Orange-Red 31A near the ends.

Sepals are permanent.

An average number of medium sized seeds are produced, around 10 to 15 in number.

FOLIAGE

The compound leaves are moderately heavy and semi-glossy and usually comprises 3 to 5, sometimes 7 leaflets. Leaves are borne in average quantities for the class. Leaflets are oval in shape, with acute apices; their bases are usually obtuse and margins are doubly serrate.

The color of the upper leaf surface is near Green 147A; the lower leaf surface is near Green 137D. New growth is near Green 143A in color, tinged with red on the upper leaf surface. The under surface of young leaves is near Green 144B in color and tinged with red.

The rachis is of average size. Its upper side is grooved with some stipitate glands on the edges. The underside is moderately prickly with stipitate glands.

Stipules are short in length for the class and narrow, having very to moderately short points which usually turn out at an angle of about 45° and are slightly recurved toward the stem.

Plants of the new variety are average in their resistance to mildew as compared with other cultivars now in commerce when grown under comparable conditions at Somis, Calif.

GROWTH

Plants of the new variety are of a tall, upright and bushy habit, and much branched. Plant growth is moderately vigorous. Canes are of average to heavy caliper for the class. The main stems are near Green 146B in color. They bear few to several large thorns which are moderately long for the class and hooked slightly downward. The thorn base is moderately short and narrow. Thorns are near Greyed-Brown 199C in color. There are no prickles and no hairs.

Branches are near Green 144A in color; they bear several to many large thorns and these are long for the class. Thorns are almost straight and have moderately narrow bases of medium length. Thorns are near Greyed-Orange 166C in color. There are no small prickles or hairs.

New shoots are near Green 138A in color, tinged with near Greyed-Red 178A. New shoots bear several to many large thorns which are of average length to long for the class. Large thorns are hooked downward and have long broad bases. Large thorns are near Yellow-Green 146D in color. There are no small prickles and no hairs.

I claim:

1. A new and distinct variety of hybrid tea rose plant cv. Arobipy, the parts thereof, being particularly characterized by its tall growing habit; its large excellently formed buds and flowers; its uniformly white blossoms with only the outer guard petals having traces of pink and green along the margin and midrib, respectively; and its broad petals numbering between thirty and thirty-five petals per blossom as described and illustrated.

* * * * *

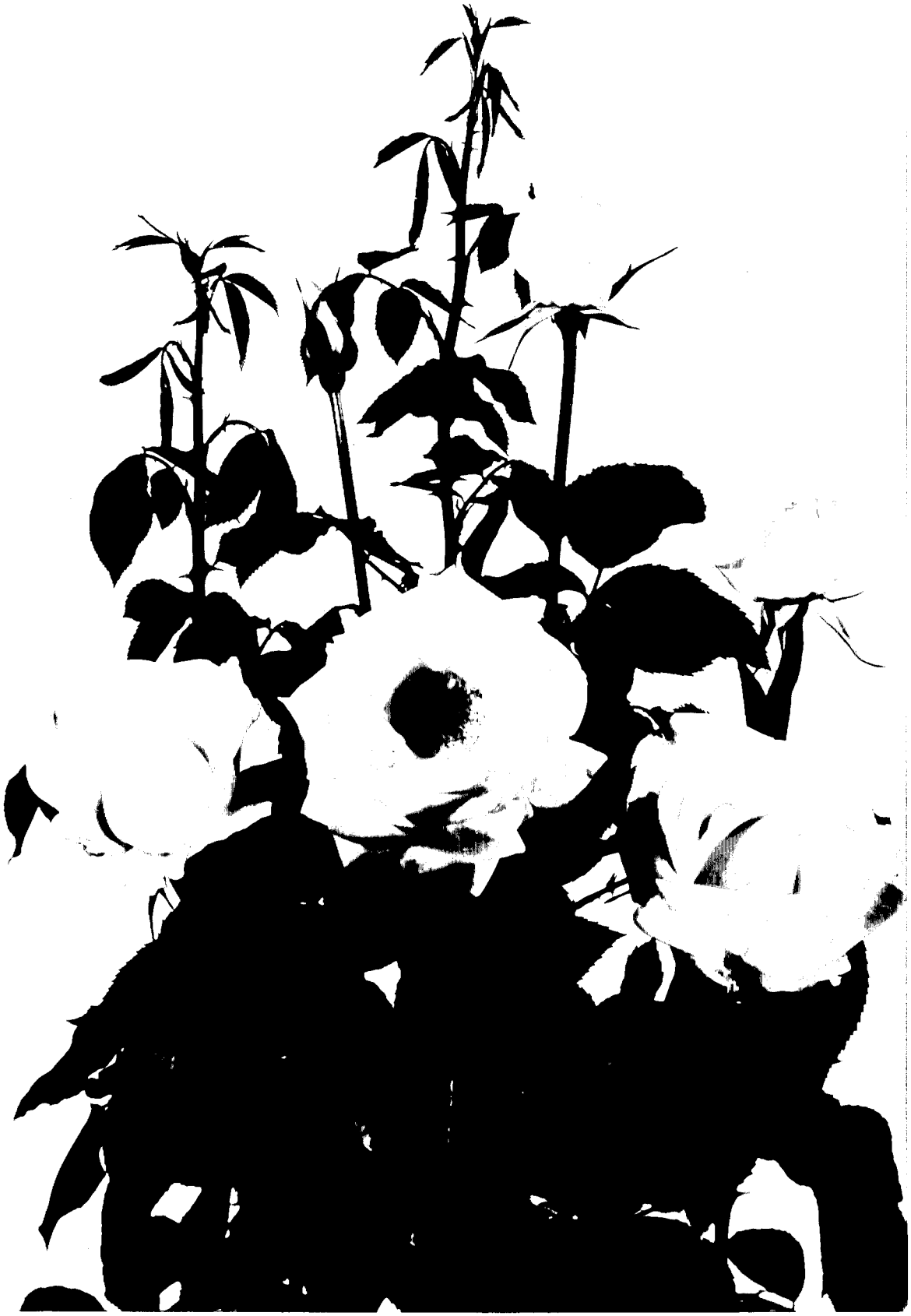

UNITED STATES PATENT AND TRADEMARK OFFICE

CERTIFICATE OF CORRECTION

PATENT NO. : Plant 6,714

DATED : April 4, 1989

INVENTOR(S) : Christensen et al

It is certified that error appears in the above-identified patent and that said Letters Patent is hereby corrected as shown below:

Column 3, line 16, "moderatley" should be --moderately--;

line 53, "6 to 7" should be --4 to 5--; and line 55, "4 to 5" should be --6 to 7--.

Signed and Sealed this

Fifth Day of December, 1989

*Attest:*

JEFFREY M. SAMUELS

*Attesting Officer*

*Acting Commissioner of Patents and Trademarks*